(12) United States Patent
Gaboardi et al.

(10) Patent No.: US 10,112,967 B2
(45) Date of Patent: Oct. 30, 2018

(54) PROCESS FOR THE PREPARATION OF SOFOSBUVIR

(71) Applicant: HC-PHARMA AG, Zug (CH)

(72) Inventors: Mauro Gaboardi, Novara (IT); Giuseppe Pallanza, Robbio (IT); Marco Baratella, Cerano (IT); Graziano Castaldi, Briona (IT); Marta Castaldi, Sizzano (IT)

(73) Assignee: HC-PHARMA AG, Zug (CH)

( * ) Notice: Subject to any disclaimer, the term of this patent is extended or adjusted under 35 U.S.C. 154(b) by 0 days.

(21) Appl. No.: 15/358,850

(22) Filed: Nov. 22, 2016

(65) Prior Publication Data
US 2017/0247404 A1    Aug. 31, 2017

(30) Foreign Application Priority Data
Feb. 25, 2016    (IT) .................. 102016000019503

(51) Int. Cl.
*C07H 19/10* (2006.01)
*C12P 19/30* (2006.01)
*C07H 1/00* (2006.01)

(52) U.S. Cl.
CPC ............... *C07H 19/10* (2013.01); *C07H 1/00* (2013.01); *C12P 19/305* (2013.01)

(58) Field of Classification Search
CPC .......... C07H 19/10; C07H 1/00; C12P 19/305
See application file for complete search history.

(56) References Cited

U.S. PATENT DOCUMENTS 7,964,580 B2    6/2011   Sofia et al.

FOREIGN PATENT DOCUMENTS

| WO | 2015017713 A1 | 2/2015 |
| WO | 2015123352 A1 | 8/2015 |

OTHER PUBLICATIONS

Hennen et al. J. Org. Chem. (1988) 53: 4989-4945 (Year: 1988).*
(Continued)

*Primary Examiner* — Susan M Hanley
(74) *Attorney, Agent, or Firm* — Lucas & Mercanti, LLP

(57) ABSTRACT

A process for the synthesis of Sofosbuvir (I)

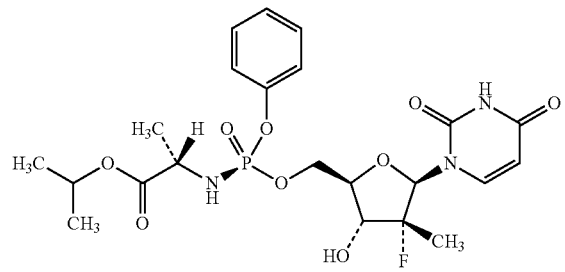

is provided comprising the steps of selectively mono-deacetylating a compound of formula (V)

(V)

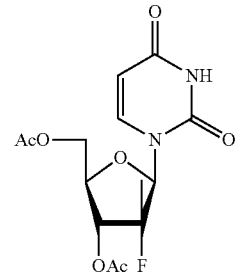

enzymatically using a resin supported lipase B derived from *Candida Antarctica* to obtain a compound formula (IV), (IV)

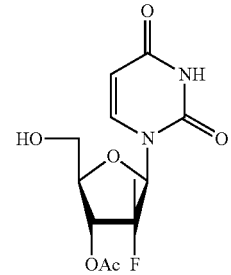

then converting the compound of formula (IV) to a compound of formula (II)

(II)

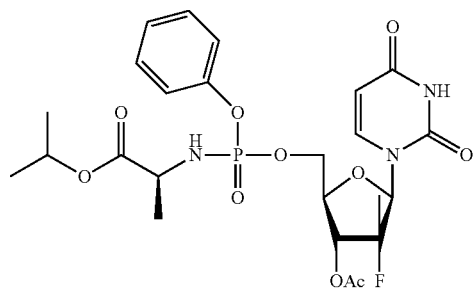

(Continued)

by reacting the compound of formula (IV) with a compound of formula (III), and

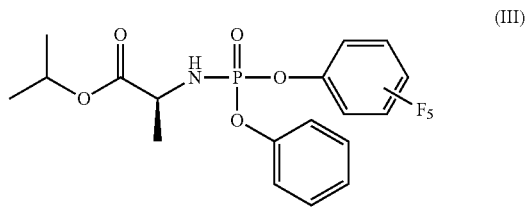

then converting the compound of formula (II) to Sofosbuvir of formula (I) by deacetylation reaction.

15 Claims, No Drawings

(56) References Cited

OTHER PUBLICATIONS

Sharma et al. Indian J. Chem. (2009) 48B: 1712-1720 (Year: 2009).*
Zinni, Marfa A., et al., Enzymatic Alcoholysis of 3' . . . , Journal of Molecular Catalysis, vol. 29, No. 1-6, 2004.
European Search Report and Written Opinion corresponding to IT UB20161079, filed Jul. 13, 2016.

* cited by examiner

PROCESS FOR THE PREPARATION OF SOFOSBUVIR

CROSS-REFERENCE TO RELATED APPLICATIONS

This application claims the benefit of priority from Italian Patent Application No. 102016000019503 (UB2016A001079) filed on Feb. 25, 2016, the contents of which are incorporated herein by reference.

FIELD OF THE INVENTION

The present invention relates to a process for the synthesis of Sofosbuvir. Sofosbuvir is a prodrug used for the treatment of hepatitis C.

BACKGROUND OF THE INVENTION

Hepatitis C is an infectious disease caused by the Hepatitis C virus (HCV), which primarily affects the liver. The infection is often asymptomatic, but its chronicity can lead to scarring of the liver and, finally, to cirrhosis, which generally becomes evident several years later. In some cases, hepatic cirrhosis may lead to develop liver failure, liver cancer, esophageal and gastric varices. HCV is spread primarily through direct contact with infected blood, often associated with intravenous drugs use, poorly sterilized medical equipments, and blood transfusions.

Hepatitis C virus leads to a chronic infection in 50-80% of HCV-positive people, 40-80% of which are treated. Generally, the pharmacological treatment is recommended in patients with hepatic alterations caused by the virus; the reference treatment is a combination of pegylated interferon alfa and ribavirin, to be taken for a period of 24 or 48 weeks, depending on the HCV virus genotype. It was observed that this therapy leads to improvements in 50-60% of the cases.

In the most difficult phenotypes to treat, these two drugs are used together with boceprevir and telaprevir, bringing the healing rate from 40% to 70%.

Side effects of the treatment are frequent, half of the patients feels flu-like symptoms and a third shows emotional problems, moreover treatment during the first six months proves to be more effective than when hepatitis C becomes chronic.

Sofosbuvir is an EMA and FDA approved drug for the treatment of hepatitis C, it is taken orally and it acts with a mechanism of action directed to the virus life cycle by disrupting its replication, since, being a pan-genotypic inhibitor of HCV RNA-dependent RNA polymerase NS5B prodrug, it can be folded into the HCV RNA of the polymerase NS5B and it can act as a chain terminator. Sofosbuvir has also shown a reduced number of liver disease complications and a reduced number of side effects, compared with patients treated with other treatments.

Sofosbuvir is a compound of formula (I)

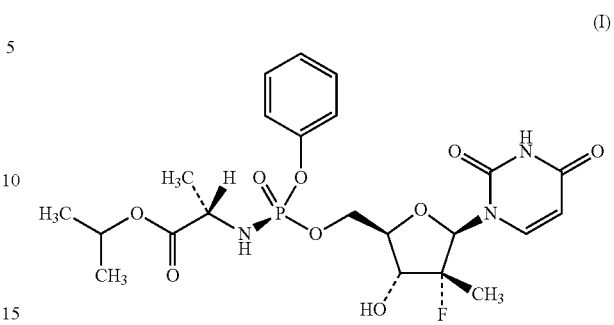

(I)

chemically known as
isopropyl (2S)-2-[[[(2R,3R,4R,5R)-5-(2,4-dioxopyrimidin-1-yl)-4-fluoro-3-hydroxy-4-methyl-tetrahydrofuran-2-yl]methoxy-phenoxy-phosphoryl]amino]propanoate, marketed as Sovaldi® and disclosed in U.S. Pat. No. 7,964,580.

U.S. Pat. No. 7,964,580 discloses a process for the preparation of Sofosbuvir of formula (I) by the reaction of a compound of formula 4", wherein X' is a leaving group, with a nucleoside analogue of formula 5'

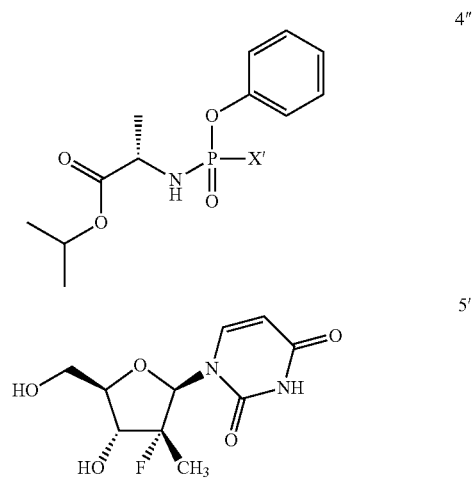

J. Org. Chem., (2011), 76, 8311-8319 discloses the following process for the synthesis of Sofosbuvir, shown in Scheme 1 and in Scheme 2:

Scheme 1

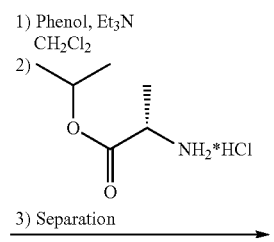

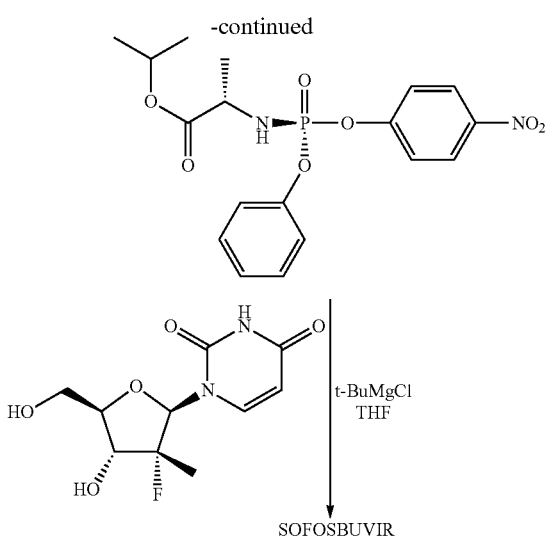

SOFOSBUVIR

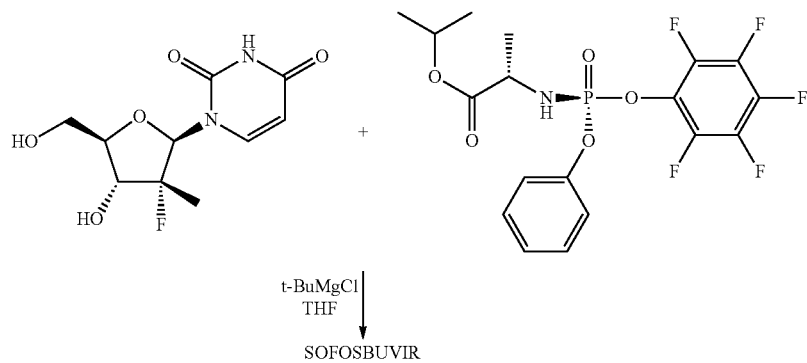

Scheme 2 t-BuMgCl
THF

SOFOSBUVIR

The processes disclosed in the the art show several drawbacks due to the presence of two hydroxyl groups in the nucleosidic intermediates reported above, particularly when a Grignard reagent was used for their salification. Said salification reaction, in fact, is non selective and therefore the reaction requires at least two equivalents of Grignard reagent resulting in a double salt which is almost insoluble in the reaction environment and which in turn makes the reaction run and its work up more difficult. Moreover, double salification leads to obtain moderate amounts of two main by-products, such as Sofosbuvir 3' isomer and the di-substituted compound in 3' and 5' position. These two by-products are difficult to separate from Sofosbuvir of formula (I) and, in order to obtain Sofosbuvir of formula (I) having a purity in compliance with the regulatory requirements, long-lasting manufacturing and purification processes are needed.

WO2015/017713 relates to a process for preparing Sofosbuvir, but it does not foresee the use of the intermediate of formula (IV) according to the present invention in the preparation of Sofosbuvir.

WO2015/123352 implicitly discloses the intermediate of formula (IV) used in the process of the present invention, but it gives no hint to use this intermediate for the synthesis of derivatives of Sofosbuvir unprotected at the 3' position.

Journal of Molecular Catalysis. B, Enzymatic, (2004), 29, 129-132 discloses the selective deprotection of the 5'-O-acetyl of different nucleosides. However, these compounds are not used in the preparation of Sofosbuvir or analogous compound thereof and, in addition, 2'-fluoro ribosides were not tested as possible substrates in D3.

DETAILED DESCRIPTION OF THE INVENTION

The inventors of the present invention have now found a new process for the synthesis of Sofosbuvir of formula (I), which overcomes all the drawbacks of the processes known in the art. The process of the present invention proves to be surprisingly advantageous since it is selective and, in particular, during said process no reaction by-products are formed such as Sofosbuvir 3' isomer and/or the di-substituted compound in 3' and 5' position. Therefore the process of the present invention allows for easily purifying and obtaining Sofosbuvir of formula (I) in high yield and purity.

Therefore an object of the present invention is a process for the synthesis of Sofosbuvir of formula (I)

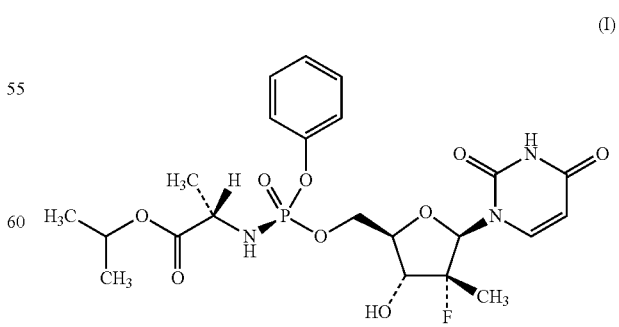

(I)

comprising the selective mono-deacetylation reaction of a compound of formula (V)

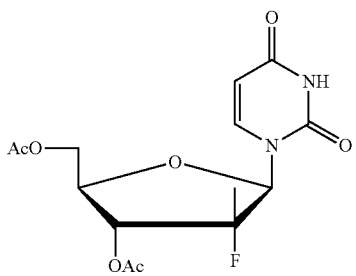

(V)

to obtain a compound of formula (IV)

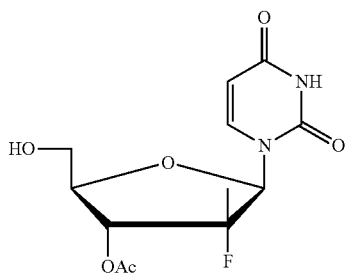

(IV)

The selective mono-deacetylation reaction of the process object of the present invention can be carried out enzymatically using a resin supported lipase, preferably deriving from *Candida Antarctica*, more preferably lipase B deriving from *Candida Antarctica* (such as for example CALB) in a polar protic solvent at a temperature from about 40° C. to about 70° C., preferably at a temperature of about 60° C.

The polar protic solvent is typically an alkanol, preferably a straight or branched $C_1$-$C_6$ alkanol selected among methanol, ethanol, isopropanol and n-butanol or a substituted alkanol selected among methoxyethanol, methoxypropanol, methoxybutanol, preferably methoxypropanol and mixtures of said solvents with water.

In a particularly preferred embodiment of the invention, the polar protic solvent is isopropanol, methoxypropanol or a mixture of ethanol and water.

The compound of formula (IV), thus obtained, can be converted to a compound of formula (II)

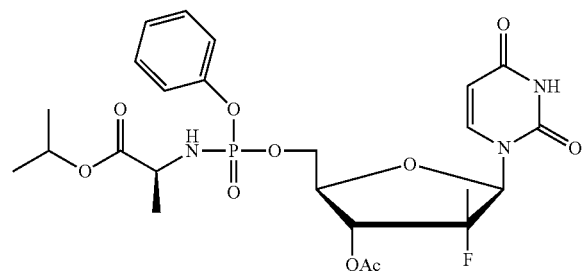

(II)

by reaction of said compound of formula (IV) with a compound of formula (III)

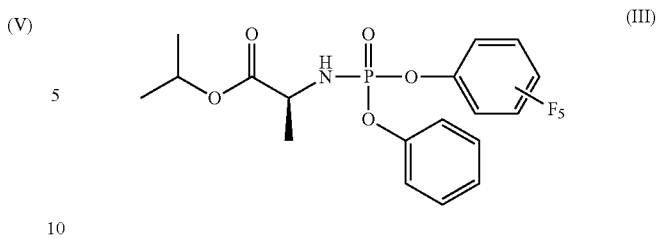

(III)

wherein $F_5$ indicates that the aromatic ring is pentafluoro substituted.

The reaction of a compound of formula (IV) with a compound of formula (III) can be carried out in the presence of a base selected among 1,5-diazabicyclo[5.4.0]undec-5-ene (DBU), 1,5,7-triazabicyclo[4.4.0]dec-5-ene (TBD), 1,4-diazabicyclo[2.2.2]octane (DABCO), preferably the base is 1,5-diazabicyclo[5.4.0]undec-5-ene (DBU).

In addition, the reaction of the compound of formula (IV) with a compound of formula (III) can be carried out in the presence of an aprotic solvent, preferably selected among dichloromethane, acetonitrile, tetrahydrofuran, acetone, dimethyl sulfoxide, more preferably tetrahydrofuran.

Said reaction can be carried out at a temperature from about −40° C. to about 40° C., preferably from about −10° C. to about 10° C., more preferably at a temperature of about 0° C.

The resultant compound of formula (II) can be then converted to Sofosbuvir of formula (I) by deacetylation reaction.

The deacetylation reaction of a compound of formula (II) can be carried out:

a) under basic catalysis conditions, with a base selected among triethylamine (TEA), 1,5-diazabicyclo[5.4.0]undec-5-ene (DBU), ethanolamine, sodium carbonate, sodium bicarbonate, or a mixture thereof, in a polar protic solvent selected among water, methanol, ethanol, propanol, isopropanol, butanol, sec-butanol and tert-butanol, or in a polar aprotic or protic solvent selected among ethyl acetate, tetrahydrofuran, dichloromethane, acetonitrile, isopropanol and a mixture of two or more of said solvents; preferably in the deacetylation reaction under basic catalysis conditions sodium carbonate in a mixture of methanol and water or ethanolamine in one or more of the above mentioned polar protic solvents is used; or b) under acid catalysis conditions, with an acid selected among hydrochloric acid, sulfuric acid, methanesulfonic acid, trifluoroacetic acid, or with catalytic acyl chloride, for example acetyl chloride, in a polar protic solvent selected among methanol, ethanol, propanol, isopropanol, butanol, sec-butanol and tert-butanol; preferably in the deacetylation reaction under acid catalysis conditions hydrochloric acid in isopropanol is used.

The deacetylation reaction of a compound of formula (II) can be carried out at a temperature from about −5° C. to about 25° C., preferably at a temperature from about −5° C. to about 5° C.

It should be noted that the compound of formula (III) is known from J. Org. Chem., (2011), 76, 8311-8319, while the compound of formula (V) is known from CN104327138 A.

All the terms used in the present application, unless otherwise indicated, must be understood in their common meaning as known in the state of the art. The term "about" comprises the experimental error range which may occur in a measurement.

Although the present invention was described in its main features, modifications and equivalents which are evident to a person skilled in the art are included in the present invention.

Hereinafter, the present invention is shown through some examples, which are to be intended as limiting the scope of the invention.

Example 1. Synthesis of (2R,3S,5R)-5-(2,4-dioxo-3, 4-dihydropyrimidin-1(2H)-yl)-4-fluoro-2-(hydroxymethyl)-4-methyltetrahydrofuran-3-yl acetate of Formula (IV)

((2R,3S,5R)-3-acetoxy-5-(2,4-dioxo-3,4-dihydropyrimidin-1(2H)-yl-4-fluoro-4-methyltetrahydrofuran-2-yl) methyl acetate (500 g, 1.45 mol) of formula (V) and isopropanol (5000 mL) were loaded into a reaction flask. The temperature was raised to about 60° C., CALB lipases (100 g) were added and the reaction mixture was maintained under these conditions for about forty-eight hours. When the reaction was completed, the temperature was brought to about 25° C., the CALB lipases were removed by filtration, the solvent was removed by vacuum distillation till a residual volume of about 900 mL and the temperature was cooled to about 0° C. The mixture was filtered, washed with isopropanol (1×250 mL) and reduced till residue by vacuum distillation to give 354 g of (2R,3S,5R)-5-(2,4-dioxo-3,4-dihydropyrimidin-1(2H)-yl)-4-fluoro-2-(hydroxymethyl)-4-methyltetrahydrofuran-3-yl acetate of formula (IV) having a HPLC purity of 99.2%.

$^1$H-NMR (DMSO, 300 MHz): δ 11.52 (s, 1H), 8.00 (d, 1H), 6.06 (d, 1H), 5.73 (d, 1H), 5.34-5.19 (m, 2H), 4.11 (d, 1H), 3.80 (d, 1H), 3.58 (d, 1H), 2.11 (s, 3H), 1.29 (d, 3H)

$^{13}$C-NMR (DMSO, 300 MHz): δ 170.2 (C), 163.4 (C), 151.1 (C), 140.7 (C), 103.0 (CH), 100.7 (C), 80.3 (CH), 71.4 (CH), 71.2 (CH), 59.0 (CH$_2$), 21.0 (CH$_3$), 17.7 (CH$_3$).

Example 2. Synthesis of (2R,3S,5R)-5-(2,4-dioxo-3, 4-dihydropyrimidin-1(2H)-yl)-4-fluoro-2-(hydroxymethyl)-4-methyltetrahydrofuran-3-yl acetate of Formula (IV)

((2R,3S,5R)-3-acetoxy-5-(2,4-dioxo-3,4-dihydropirimidin-1(2H)-yl-4-fluoro-4-methyltetrahydrofuran-2-yl)methyl acetate (500 g, 1.45 mol) of formula (V) and methoxypropanol (5000 mL) were loaded into a reaction flask. The temperature was raised to about 60° C., CALB lipases (100 g) were added and the reaction mixture was maintained under these conditions for about forty-eight hours. When the reaction was completed, the temperature was brought to about 25° C., CALB lipases were removed by filtration, the solvent was removed by vacuum distillation till a residual volume of about 900 mL and the temperature was brought to about 0° C. The mixture was filtered, washed with methoxypropanol (1×250 mL) and reduced till residue by vacuum distillation to give 346 g (2R,3S,5R)-5-(2,4-dioxo-3,4-dihydropyrimidin-1(2H)-yl)-4-fluoro-2-(hydroxymethyl)-4-methyltetrahydrofuran-3-yl acetate of formula (IV) having a HPLC purity of 99.5%.

$^1$H-NMR (DMSO, 300 MHz): δ 11.52 (s, 1H), 8.00 (d, 1H), 6.06 (d, 1H), 5.73 (d, 1H), 5.34-5.19 (m, 2H), 4.11 (d, 1H), 3.80 (d, 1H), 3.58 (d, 1H), 2.11 (s, 3H), 1.29 (d, 3H)

$^{13}$C-NMR (DMSO, 300 MHz): δ 170.2 (C), 163.4 (C), 151.1 (C), 140.7 (C), 103.0 (CH), 100.7 (C), 80.3 (CH), 71.4 (CH), 71.2 (CH), 59.0 (CH$_2$), 21.0 (CH$_3$), 17.7 (CH$_3$).

Example 3. Synthesis of (2R,3S,5R)-5-(2,4-dioxo-3, 4-dihydropyrimidin-1(2H)-yl)-4-fluoro-2-(hydroxymethyl)-4-methyltetrahydrofuran-3-yl acetate of Formula (IV)

((2R,3S,5R)-3-acetoxy-5-(2,4-dioxo-3,4-dihydropyrimidin-1(2H)-yl-4-fluoro-4-methyltetrahydrofuran-2-yl)methyl acetate (500 g, 1.45 mol) of formula (V), ethanol (5000 mL) and water (500 mL) were loaded into a reaction flask. The temperature was brought to about 60° C., CALB lipases (100 g) were added and the reaction mixture was maintained in these conditions for about forty-eight hours. When the reaction was completed, the temperature was brought to about 25° C., CALB lipases were removed by filtration, the solvent was removed by vacuum distillation till a residual volume of about 900 mL and the temperature was brought to about 0° C. The mixture was filtered, washed with methoxypropanol (1×250 mL) and reduced till residue by vacuum distillation to give 331 g of (2R,3S,5R)-5-(2,4-dioxo-3,4-dihydropyrimidin-1(2H)-yl)-4-fluoro-2-(hydroxymethyl)-4-methyltetrahydrofuran-3-yl acetate of formula (IV), having a HPLC purity of 99.6%.

$^1$H-NMR (DMSO, 300 MHz): δ 11.52 (s, 1H), 8.00 (d, 1H), 6.06 (d, 1H), 5.73 (d, 1H), 5.34-5.19 (m, 2H), 4.11 (d, 1H), 3.80 (d, 1H), 3.58 (d, 1H), 2.11 (s, 3H), 1.29 (d, 3H)

$^{13}$C-NMR (DMSO, 300 MHz): δ 170.2 (C), 163.4 (C), 151.1 (C), 140.7 (C), 103.0 (CH), 100.7 (C), 80.3 (CH), 71.4 (CH), 71.2 (CH), 59.0 (CH$_2$), 21.0 (CH$_3$), 17.7 (CH$_3$).

Example 4. Synthesis of (2S)-isopropyl-2-(M2R,3S, 5R)-3-acetoxy-5-(2,4-dioxo-3,4-dihydropyrimidin-1 (2H)-yl)-4-methyltetrahydrofuran-2 yl)methoxy) (phenoxy)phosphorylamino)propanoate of Formula (II)

(2R,3S,5R)-5-(2,4-dioxo-3,4-dihydropyrimidin-1(2H)-yl)-4-fluoro-2-(hydroxymethyl)-4-methyltetrahydrofuran-3-yl acetate (300 g, 0.992 mol) of formula (IV) as obtained in example 1, tetrahydrofuran (2000 mL), (2S)-isopropyl-2-((perfluorophenoxy)(phenoxy)phosphorylamino)propanoate (495 g, 1.091 mol) of formula (III) were loaded into a reaction flask, the temperature was brought to about 0° C., 1,5-diazabicycle[5.4.0]undec-5-ene (DBU, 166 g, 1.091 mol) was added and the reaction mixture was maintained in these conditions for about three hours. When the reaction was completed, the temperature was brought to 20° C., the solvent was removed by vacuum distillation, dichloromethane was added (3000 mL) and the mixture was washed with a solution of 1N hydrochloric acid (2×1000 mL). The organic layers were washed with an aqueous solution of 10% sodium carbonate (4×1000 mL), a solution of 1N hydrochloric acid (1×1000 mL), water (1×1000 mL), filtered and the aqueous layer was extracted with dichloromethane (1×1000 mL). The combined organic layers were reduced to residue by vacuum distillation to give 510.5 g of (2S)-isopropyl-2-(((((2R,3S,5R)-3-acetoxy-5-(2,4-dioxo-3,4-dihydropyrimidin-1(2H)-yl)-4-fluoro-4-methyltetrahydrofuran-2-yl)methoxy) (phenoxy)phosphorylamino) propanoate of formula (II) having a HPLC purity of 89.2%.

$^1$H-NMR (DMSO, 300 MHz): δ 9.50 (s, 1H), 7.52 (d, 1H), 7.32-7.28 (m, 2H), 7.22-7.19 (m, 3H), 6.18 (d, 1H), 5.52 (d, 1H), 5.21-5.12 (m, 1H), 5.04-4.93 (m, 1H), 4.56-4.48 (m, 1H), 4.31-4.18 (m, 2H), 4.15-3.94 (m, 2H), 2.16 (s, 3H), 1.43-1.29 (m, 6H), 1.21 (d, 6H).

Example 5. Synthesis of Sofosbuvir of Formula (I)

(2S)-isopropyl-2-(((((2R,3S,5R)-3-acetoxy-5-(2,4-dioxo-3,4-dihydropyrimidin-1(2H)-yl)-4-fluoro-4-methyltetrahydrofuran-2-yl)methoxy)(phenoxy) phosphorylamino) propanoate (100 g, 0.175 mol) of formula (II) as obtained in example 4, methanol (300 mL), water (300 mL) were loaded into a reaction flask and the temperature was brought to about 5° C. Sodium carbonate (20.85 g, 0.197 mol) was added and the mixture was maintained under these conditions for about twenty hours.

When the reaction was completed, water (200 mL), dichloromethane (250 mL) were added, the temperature was brought to about 25° C. and the aqueous layers were extracted with dichloromethane (2×250 mL). The combined organic layers were washed with a solution of 2% sodium bicarbonate (1×200 mL), hydrochloride acid (1×200 mL), water (1×200 mL), filtered and distilled under vacuum till an internal volume of about 350 mL. The temperature was brought to about 0° C., the solid formed was filtered, cold washed with dichloromethane (2×30 mL) and dried in vacuum oven at 40° C. to give 71 g of Sofosbuvir of formula (I) having a HPLC purity of 99.6%.

Example 6. Synthesis of Sofosbuvir of Formula (I)

(2S)-isopropyl-2-((((2R,3S,5R)-3-acetoxy-5-(2,4-dioxo-3,4-dihydropyrimidin-1(2H)-yl)-4-fluoro-4-methyltetrahydrofuran-2yl)methoxy)(phenoxy)phosphorylamino) propanoate (556.9 g, 0.992 mol) of formula (II) as obtained in example 4, isopropanol (5670 mL) were loaded into a reaction flask and the temperature was brought to about 22° C. Ethanolamine was added (605.9 g, 9.920 mol) and the mixture was left under these conditions for about fourteen hours. When the reaction was completed, the temperature was brought to about 0° C., water (2830 mL), 37% hydrochloric acid (745.6 mL), were added, the temperature was brought to about 25° C. and the solvent was removed by vacuum distillation. Dichloromethane (3400 mL) was added, the organic layer was washed with a solution of 2% sodium bicarbonate (1×1200 mL), a solution of 2N sodium chloride (1×1200 mL), filtered and distilled under vacuum till an internal volume of about 2500 mL. The temperature was brought to about 0° C., the solid formed was filtered, cold washed with dichloromethane (2×300 mL) and dried in vacuum oven at 40° C. to give 324.9 g of Sofosbuvir of formula (I) having a HPLC purity of 99.5%.

Example 7. Synthesis of Sofosbuvir of Formula (I)

(2S)-isopropyl-2-((((2R,3S,5R)-3-acetoxy-5-(2,4-dioxo-3,4-dihydropyrimidin-1(2H)-yl)-4-fluoro-4-methyltetrahydrofuran-2yl) methoxy) (phenoxy) phosphorylamino) propanoate (100 g, 0.175 mol) of formula (II) as obtained in example 4, isopropanol (1000 mL) were loaded into a reaction flask, the temperature was brought to about −5° C., hydrochloridric acid was added (172 g, 1.750 mol) and the reaction mixture was maintained under these conditions for about twenty-four hours.

When the reaction was completed, water (300 mL), sodium carbonate (111 g) were added, the solvent was removed by vacuum distillation and dichloromethane was added (600 mL). The organic layer was washed with a solution of 2% sodium bicarbonate (1×200 mL) and the aqueous layers were extracted with dichloromethane (1×250 mL). The combined organic layers were washed with, hydrochloric acid (1×200 mL), water (1×200 mL), filtered and extracted with dichloromethane (3×50 mL), filtered and distillated under vacuum till an internal volume of about 350 mL. The temperature was raised to about 0° C., the solid formed was filtrated, cold washed with dichloromethane (2×30 mL) and dried in vacuum oven at 40° C. to give 69 g of Sofosbuvir of formula (I) having a 99.7% purity.

The invention claimed is:

1. A process for the synthesis of Sofosbuvir of formula (I)

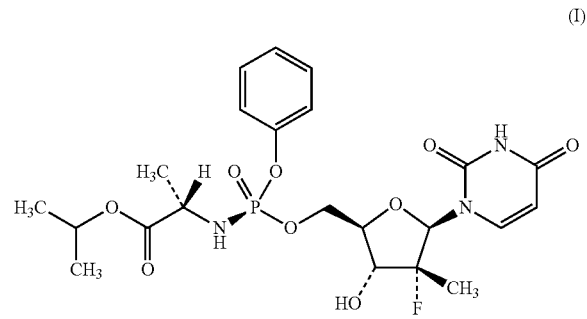 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

comprising selectively mono-deacetylating a compound of formula (V)

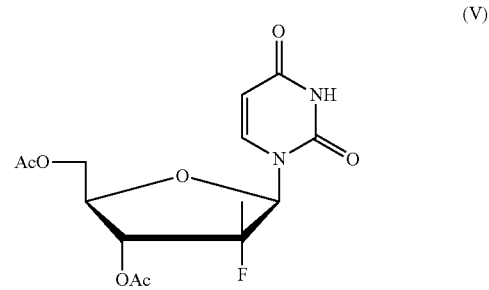

enzymatically using a resin supported lipase B derived from *Candida Antarctica* in a polar protic solvent at a temperature from 40° C. to 70° C. to obtain a compound of formula (IV)

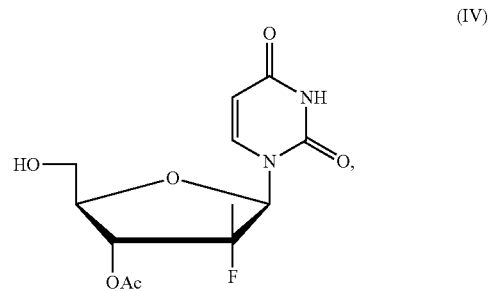

converting the compound of formula (IV) to a compound of formula (II)

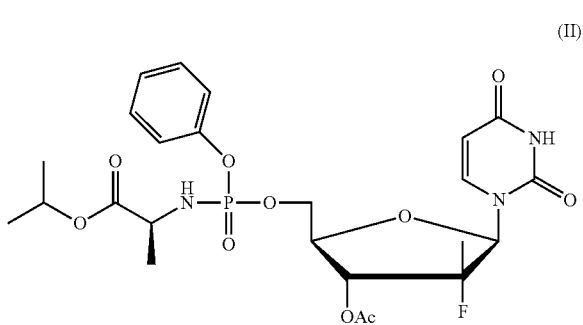

by reacting the compound of formula (IV) with a compound of formula (III)

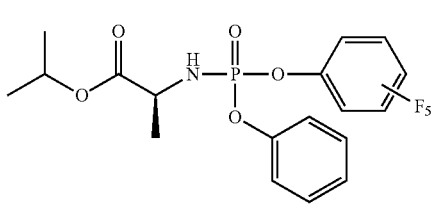

wherein F₅ indicates that the aromatic ring is pentafluoro substituted, and converting the compound of formula (II) to Sofosbuvir of formula (I) by deacetylation reaction.

2. The process according to claim 1 wherein the temperature is 60° C.

3. The process according to claim 1 wherein the polar protic solvent is an alkanol or a substituted alkanol selected from the group consisting of methoxyethanol, methoxypropanol, methoxybutanol, and mixtures of said solvents with water.

4. The process according to claim 3 wherein the alkanol is a straight or branched $C_1$-$C_6$ alkanol selected from the group consisting of methanol, ethanol, isopropanol and n-butanol.

5. The process according to claim 3 wherein the substituted alkanol is methoxypropanol.

6. The process according to claim 3 wherein the polar protic solvent is selected from the group consisting of isopropanol, methoxypropanol and a mixture of ethanol and water.

7. The process according to claim 1 wherein the reacting of the compound of formula (IV) with the compound of formula (III) is carried out in the presence of a base selected from the group consisting of 1,5-diazabicyclo[5.4.0]undec-5-ene (DBU), 1,5,7-triazabicyclo[4.4.0]dec-5-ene (TBD) and 1,4-diazabicyclo[2.2.2]octane (DABCO).

8. The process according to claim 1 wherein the reacting of the compound of formula (IV) with the compound of formula (III) is carried out in the presence of an aprotic solvent.

9. The process according to claim 8 wherein the aprotic solvent is selected from the group consisting of dichloromethane, acetonitrile, tetrahydrofuran, acetone, and dimethyl sulfoxide.

10. The process according to claim 8 wherein the aprotic solvent is tetrahydrofuran.

11. The process according to claim 1 wherein the reacting of the compound of formula (IV) with the compound of formula (III) is carried out at a temperature from −40° C. to 40° C.

12. The process according 15 wherein the temperature is from −10° C. to 10° C.

13. The process according to claim 1 wherein the deacetylating reaction of the compound of (II) is carried out:
    a) under basic catalysis conditions, with a base selected from the group consisting of triethylamine (TEA), 1,5-diazabicyclo[5.4.0]undec-5-ene (DBU), ethanolamine, sodium carbonate, sodium bicarbonate, and mixtures thereof, in a polar protic solvent selected from the group consisting of water, methanol, ethanol, propanol, isopropanol, butanol, sec-butanol and tert-butanol, or in a polar aprotic or protic solvent selected from the group consisting of ethyl acetate, tetrahydrofuran, dichloromethane, acetonitrile, isopropanol and mixtures of two or more of said solvents; or
    b) under acid catalysis conditions with an acid selected from the group consisting of hydrochloric acid, sulfuric acid, methanesulfonic acid, and trifluoroacetic acid, or with catalytic acyl chloride, in a polar protic solvent selected from the group consisting of methanol, ethanol, propanol, isopropanol, butanol, sec-butanol and tert-butanol.

14. The process according to claim 13 wherein the deacetylation reaction is carried out under acid catalysis conditions with hydrochloric acid in isopropanol.

15. The process according to claim 13 wherein the deacetylation reaction is carried out at a temperature from −5° C. to 25° C.

* * * * *